United States Patent
Moroni

(12) 
(10) Patent No.: US 6,537,467 B1
(45) Date of Patent: Mar. 25, 2003

(54) IMMOBILIZED FREE RADICAL CAPTORS

(75) Inventor: Marc Moroni, Melun (FR)

(73) Assignee: Corning Incorporated, Corning, NY (US)

(*) Notice: Subject to any disclaimer, the term of this patent is extended or adjusted under 35 U.S.C. 154(b) by 0 days.

(21) Appl. No.: 09/300,893

(22) Filed: Apr. 28, 1999

(30) Foreign Application Priority Data

Dec. 22, 1998 (FR) .............................................. 98 16212

(51) Int. Cl.[7] .............................................. C09K 15/32
(52) U.S. Cl. ........................... 252/400.31; 252/182.29; 252/183.12; 252/397; 252/399; 252/400.3; 252/404; 252/405; 252/406; 560/2
(58) Field of Search .............................. 252/400.3, 404, 252/405, 397, 399, 406, 400.31, 182.29, 183.12; 526/82, 204, 83, 84, 85; 560/2

(56) References Cited

U.S. PATENT DOCUMENTS

| | | | | |
|---|---|---|---|---|
| 3,136,729 A | * | 6/1964 | Clark | 526/194 X |
| 4,104,196 A | * | 8/1978 | Zaffaroni | 252/404 |
| 4,414,370 A | * | 11/1983 | Hamielec et al. | 526/88 |
| 4,783,294 A | * | 11/1988 | Kimura et al. | 264/45.3 |
| 4,888,375 A | | 12/1989 | Greco et al. | 524/262 |
| 4,946,880 A | | 8/1990 | Constanzi et al. | 524/96 |
| 5,721,320 A | * | 2/1998 | Priddy et al. | 526/204 X |
| 5,998,555 A | * | 12/1999 | Vijayaraghavan et al. | 526/204 |

FOREIGN PATENT DOCUMENTS

| | | |
|---|---|---|
| JP | 61-100587 | 5/1986 |

OTHER PUBLICATIONS

Rubber Technology, 3rd ed., Van Nostrand Reinhold, N.Y., pp. 86, 94 (1987).*
L.B. Levy in Journal of Polymer Science; Polymer Chemistry, 23, 1505 (1985) and 30, 569 (1992) (methoxyphenol, phenothiazine, acrylic acid monomer).
L.B. Levy in Journal of Applied Polymer Science, 60, 2481 (1996) (methoxyphenol, butyl acrylate).
S.S. Cutié, D.E. Henton, C. Powell, R.E. Reim, P.B. Smith, T.L. Staples, in Journal of Applied Polymer Science, 64, 577 (1997) (methoxyphenol, acrylic acid).
Encyclopaedia of Polymer Science and Engineering, $2^{nd}$ edition, vol. 13, p. 729–735, Ed Wiley Interscience (1988) (para–benzoquinone, DPPH, metal salts, acrylates, methacrylates, acrylonitrile, styrene.

* cited by examiner

*Primary Examiner*—Fred Teskin
(74) *Attorney, Agent, or Firm*—Peter Rogalskyj; Angela N. Nwaneri; Thomas R. Beall

(57) ABSTRACT

The present invention relates to free radical captors, especially to radical polymerization inhibitors or retarders which, characteristically, are immobilized on a solid support. The present invention also relates to a method of preparing said immobilized captors, and to a method of stabilizing, at least temporarily, molecules or mixtures of molecules which makes use of said immobilized captors.

21 Claims, No Drawings

IMMOBILIZED FREE RADICAL CAPTORS

The present invention relates to immobilized free radical captors, to their preparation and to their use. More specifically, the present invention relates to:

- immobilized free radical captors, and especially immobilized radical polymerization inhibitors or retarders;
- a method of preparing them; and
- a method of stabilizing, at least temporarily, molecules or mixtures of molecules, which makes use of said immobilized captors.

According to prior art, free radical captors are used per se in various contexts for protecting molecules which are sensitive to free radicals, from said free radicals. They are suitable, for example:

- as stabilizers or preservatives: placed in the presence of sensitive molecules, such as biological molecules (for example, polyunsaturated lipids, vitamins), they minimize the degradation of the sensitive molecules by said radicals;
- as radical polymerization inhibitors or retarders: dispersed within monomers, they prevent any uncontrolled and/or premature polymerization thereof (especially during phases of storage and transport of said monomers). Such radical polymerization inhibitors or retarders (methoxyphenol, phenothiazine, para-benzoquinone, 2,2-diphenyl-1-picrylhydrazyl (DPPH), metal salts) and their mechanisms of action (in the presence of monomers such as acrylic acid, butyl acrylate, acrylonitrile, styrene, even more generally, acrylates and methacrylates) have notably been described:
  - by L. B. Levy in Journal of Polymer Science; Polymer Chemistry, 23, 1505 (1985) and 30, 569 (1992) (methoxyphenol, phenothiazine, acrylic acid monomer);
  - by L. B. Levy in Journal of Applied Polymer Science, 60, 2481 (1996) (methoxyphenol, butyl acrylate);
  - by S. S. Cutié, D. E. Henton, C. Powell, R. E. Reim, P. B. Smith, T. L. Staples, in Journal of Applied Polymer Science, 64, 577 (1997) (methoxyphenol, acrylic acid); and
  - in Encyclopaedia of Polymer Science and Engineering, $2^{nd}$ edition, vol. 13, p. 729–735, Ed Wiley Interscience (1988) (para-benzoquinone, DPPH, metal salts, acrylates, methacrylates, acrylonitrile, styrene . . . ).

Thus, the commercially available liquid monomers, especially those of the vinylic type (acrylates, or styrene, for example) usually contain 50 to 1,500 ppm of dissolved inhibitor(s) or retarder(s). Said inhibitor(s) or retarder(s) rapidly react with any free radical which is spontaneously generated at ambient temperature and/or under the action of light.

According to a first variant, such molecules prevent any efficient polymerization, and it is imperative to get rid of them when it is desired to initiate said polymerization. Their prior and compulsory removal, by distillation or chromatography, is a relatively difficult technique to carry out, especially on an industrial scale. The complete removal is in any case only with difficulty.

According to a second variant, molecules of this type are only active as inhibitors or retarders up to a certain temperature threshold and/or up to a certain irradiation threshold. It is necessary to, pass over this threshold in order to initiate the polymerization desired in the presence of said molecules. In such a context, said polymerization, deferred with time, is slower to carry out, more difficult to control and, in any case, it generates a polymer which contains said molecules as impurities.

The presence of these molecules in the monomers is furthermore cumbersome or restricting, for various reasons. Thus

- in order to maintain a certain constancy in the process of polymerization, especially in its kinetics, it proves to be compulsory to keep the concentration of said molecules constant. The latter, obviously, decreases with time: the longer the storage time is, the more significant the amount of inhibitor(s) or retarder(s) consumed is. Maintaining said amount constant is a real constraint;
- certain inhibitors or retarders, such as hydroquinone or methoxyphenol, only react with the free radicals in the presence of oxygen. It is however difficult to ensure a homogeneous dissolved oxygen content within a mixture of monomers. Failing this, the polymer obtained by polymerization of said mixture will not have a perfect homogeneity. The Applicant is especially confronted with this technical problem during the preparation of photochromic or non-photochromic lenses; the leak-tightness at the joint of the lens mould is never perfect;
- said inhibitor molecules may induce parasitic reactions with various types of other molecules (photochromic or non-photochromic colorants, chromophores . . . ), which may be present in the mixture to be polymerised;
- said inhibitor molecules can also directly influence the final properties of the polymer prepared. Thus, they may alter the optical properties thereof. For a typical concentration of 100 ppm of said inhibitor molecules in the mixture to be polymerised, said molecules, which contain C—H and C—OH groups, increase the loss of transmission at 1.55 µm, by about 0.1 dB/cm in the polymerised material . . .

Upon considering all the problems set forth above, the Applicant desired developing an alternative to the use in accordance with prior art of dissolved free radical captors. The Applicant proposes to no longer use said dissolved free radicals captors per se, but to make them immobilized on a solid support. Thus, whatever their nature and the context of their use may be, they can be easily manipulated, in general got rid of, prior to the implementation of the polymerization, in the particular case of radical polymerization inhibitors or retarders.

Thus, according to a first object, the presently claimed invention relates to free radical captors, especially radical polymerization inhibitors or retarders within the sense of the prior art which, characteristically, are immobilized on a solid support.

Said free radical captors, especially of the stabiliser type (preservative type) or polymerization inhibitor or retarder are, according to the invention, fixed in a stable manner onto a solid support.

Advantageously, the radical polymerization inhibitors or retarders are selected from:

- phenol derivatives, and especially:
  - alkylphenols, such as 2,6-di-tert-butyl-4-methylphenol,
  - hydroquinone,
  - alkoxyphenols, such as methoxyphenol,
  - catechol and derivatives thereof, such as 4-tert-butylcatechol;
- quinones and especially benzoquinone;
- phenothiazine;
- organic radicals known as stable organic radicals, and especially:

nitroxy radicals, such as 2,2,6,6-tetramethylpiperidinooxy (TEMPO), 2,2-diphenyl-1-picrylhydrazyl (DPPH);

nitro derivatives, and especially:

nitromethane, nitrobenzene;

metal salts, and especially:

$CuBr_2$, $FeCl_3$, both used in solution, advantageously in dimethylformamide (DMF);

sulphur derivatives, used in iniferter systems.

These radical polymerization inhibitors or retarders are known per se. Within the context of the present invention, it is proposed to use them in an original manner, i.e. immobilized on a support.

The most-used radical polymerization inhibitors or retarders to this day are phenol derivatives and stable organic radicals. According to a preferred variant, the free radical captors, immobilized in the sense of the invention, consist of said phenol derivatives or said stable organic radicals.

The solid support which intervenes can be of any nature. Obviously, it must be suitable for the stable immobilization of the captor on its surface, as well as for the further use of said immobilized captor. Generally, it is a mineral and/or organic support, more frequently a mineral or organic support, and, preferably, a mineral support.

An organic support, either by nature or after chemical modification of its surface, possesses on said surface numerous reactive functions, notably of the alcohol-, amine-, carboxylic acid-, halide-, ester-, amide-type . . . These reactive functions are advantageously used for the immobilization (coupling), generally by chemical grafting, of the captors.

The intervention of a:

silica support or silica-based glass support (containing more than 50% by weight of silica);

an alumina support, or an iron oxide support, titanium oxide support . . . is recommended as mineral support.

This list is not exhaustive.

The immobilization of the captor on such mineral supports is generally carried out via a covalent bond, via silanes, boranes, zirconates, alumino-zirconates, titanates, or equivalents. A chemical grafting is more particularly recommended, via a silane, on a silica support or a silica-based support.

The intervening solid support can furthermore have various forms. These can notably be particles, recipient walls, or detachable structures . . .

Thus, according to the invention, the free radical captor is advantageously immobilized on particles which are intended to intervene dispersed in liquids. Said particles are advantageously as fine as possible and also advantageously have a surface/volume ratio (a specific surface) as great as possible. However, their size must be sufficient, on the one hand, in order to enable the immobilization of the captor at their surface easily, and on the other hand, in order also to easily enable their physical separation (for example, by filtration or centrifugation) from the liquid medium in which, dispersed, they exert their action (notably as radical polymerization inhibitor). Thus, said particles generally have a size between 20 nm and 50 $\mu$m, advantageously between 200 nm and 1 $\mu$m.

The person skilled in the art has already grasped the interest of this variant of the invention. Such particles, on the surface of which free radical captors are immobilized, are perfectly suitable for the stabilization of monomers (stored, transported) awaiting polymerization. When it is desired to carry out said polymerization, it is easy to remove said particles, much easier to remove said particles than the free radical captors which intervene per se, according to prior art.

The free radical captors can also intervene, as indicated above, on the walls of a recipient. Inside said recipients, the products which are sensitive to free radicals can thus be protected. Such recipients can notably consist of reactors (within which, for example, it is desired to functionalise the molecules, notably monomers, protected from free radicals), storage reservoirs, transport reservoirs, piping or analogues. It can prove to be particularly interesting to have effective captors immobilized onto the internal walls of piping.

The concept of the invention—immobilization of free radicals—can also be developed according to another variant: said free radical captors intervening immobilized on detachable structures. Said free radical captors are therefore of great flexibility of use. The detachable structure can, as much as is desired, be introduced and then taken out of the medium in which the immobilized free radical captors must exert their action. The detachable structure can notably be successively introduced and then taken out of recipients of the type set forth above. Said detachable structure advantageously has a significant specific surface (a surface/volume ratio). Advantageously, it is a cellular and/or porous structure.

The concept of the invention can therefore avail itself according to numerous variants, notably with reference to the nature and the form of the intervening support.

It is now proposed to specify, in a totally non-limiting way, how the free radical captors can, according to the invention, be immobilized onto the solid support. In the absolute, any type of stable coupling is suitable. Obviously, it is suitable to conserve, during use, the captor immobilized on the support in order not to come up against the problems encountered according to prior art with dissolved captors.

The free radical captor immobilized according to the invention onto the solid support can especially be linked to said support:

via a covalent bond, or via weaker bonds, such as ionic bonds, hydrogen bonds . . .

The first of these variants is particularly preferred, i.e. a chemical grafting (via a covalent bond). Said chemical grafting may or may not make use of a coupling agent.

In this context of chemical grafting, i.e. by making use of a covalent bond, the captor/support bond can even be developed according to numerous variants, such as:

a direct grafting of said captor onto the non-treated, non-modified surface of said support;

a direct grafting of said captor onto the surface of said support having undergone a surface treatment (for example: plasma treatment or chemical treatment of the oxidation type or others);

an indirect grafting of said captor onto the surface of said support, the surface being optionally treated; said indirect grafting making use of a coupling agent; it being possible for various types of coupling agent to be used, notably "short" coupling agents and "long" coupling agents, which are intrinsically long or which make use of a spacer . . .

The person skilled in the art upon considering the nature of the support and the nature of the captor knows how to carry out efficient chemical graftings.

As has been indicated already:

the reactive functions of the alcohol-, amine-, carboxylic acid-, halide-, ester-, amide-type . . . , of organic supports are advantageously made use of for such chemical graftings;

coupling agents of the silane-, borane-, zirconate-, alumino-zirconate-, and titanate-type are themselves advantageously used for captor/mineral support chemical graftings.

Whatever the type of support, the use of a spacer is generally prioritised, insofar as the captor, grafted via a "long" coupling agent, gains mobility and is therefore thus capable of best expressing its properties. The optimal expression of said properties can obligatorily be required in certain contexts. It is generally as such of the radical polymerization inhibitors or retarders used for stabilizing difunctional monomers; difunctional monomers such as divinylbenzene, which are more sensitive to free radicals than monofunctional monomers such as (meth)acrylates.

Generally, when a coupling agent is made use of, the immobilization of the captor on the surface of the support is carried out in two steps:

either the captor and the coupling agent are firstly joined, and then secondly, said coupling agent, joined to said captor is grafted onto the surface of the support:

or the coupling agent is firstly grafted onto the surface of the support, and then secondly, the captor is joined to said coupling agent grafted onto said support.

In the context of an advantageous variant of the invention, the captor is immobilized by chemical grafting (via a covalent bond), onto a silica support or a silica-based glass support (vide supra); a coupling agent, advantageously of the silane type, joining said captor to said support.

The captor immobilized in the sense of the invention can be schematized thus:

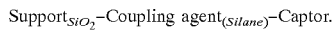

Support$_{SiO_2}$–Coupling agent$_{(Silane)}$–Captor.

Said coupling agent of the silane type or non-silane type, joined or not joined to the captor, has in general been grafted onto the surface of the support by condensation (grafting technique, per se, familiar to the person skilled in the art).

This same type of chemical reaction—condensation— may be carried out with other coupling agents (vide supra) onto surfaces of the silica type or silica-based type, even onto other types of surface (based on other metal oxides).

Purely as an illustration, coupling agents which are advantageously used according to the invention for immobilizing free radical captors onto a silica or silica-based mineral support can be listed below:

silicon tetrachloride (SiCl$_4$), alone: short coupling agent;

tetramethoxysilane (Si(OCH$_3$)$_4$), alone: short coupling agent;

silicon tetrachloride (SiCl$_4$)+bromopropanol (CH$_2$Br—CH$_2$—CH$_2$OH): long coupling agent (short coupling agent+spacer);

glycidoxypropyl trimethoxysilane

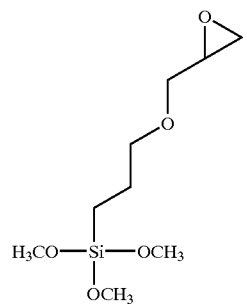

intrinsically long coupling agent.

It is recalled here that the intervention of "long" coupling agents is generally prioritised. This remark applies more particularly to silane-type coupling agents.

Thus, within the context of the advantageous variant of the invention specified above, the free radical captor is preferably capable of linking to the silica of the support by a group comprising a chain having at least three atoms different from silicon, a chain of the type:

—Si—O—C—C . . . , or

—Si—C—C—C . . .

The use of a spacer between the Si of the coupling agent and the free radical captor is more particularly recommended. Thus, advantageously, said captor can be grafted onto the silica via a group of the second of the types above, i.e. of the —Si—C—C—C— type . . . ; insofar as the Si—C— bonds are more resistant to hydrolysis than the Si—O bonds. This remark is of course valid whatever the length of the group may be.

It is recalled here that the person skilled in the art will perfectly master the chemistry which enables carrying out the graftings of the various types set forth above.

According to a second object, the present invention relates to a method of preparing said immobilized free radical captors. Said method comprises immobilizing, advantageously via a chemical grafting, either directly or via a coupling agent, said captor onto the surface of a solid support having adequate reactive groups.

It has been seen above that said immobilization can be carried out according to numerous variants, said variants obviously being adapted to the nature of said solid support. It has especially been seen that when said immobilization results from a chemical grafting, it is advantageously carried out by making use of a coupling agent, especially of a silane; said coupling agent being condensed onto the surface of the support. Details on this aspect of the method of the invention are given above, during the description of the product arising from said method: the grafted captor.

Finally, according to a third object, the present invention relates to the use of said grafted captor, namely a method of stabilizing, at least temporarily, molecules or mixtures of molecules which are sensitive to free radicals. Said method comprises placing, at least temporarily, said molecules or mixtures of molecules in contact with an effective amount of at least one grafted free radical captor. It is of course understood that in general, several free radical captors intervene which may be of the same nature or not . . .

The following is specified with reference to the expression "at least temporarily" as used above. It is of course obvious that the invention was developed for a use to a temporary stabilization end. The introduction to the present text may be referred to. It is however also obvious that the use of the captors immobilized in the sense of the invention is not excluded for "definitive" protection ends (throughout the whole of the life of the product protected).

Said process, the third object of the presently claimed invention, may avail itself according to numerous variants, and in numerous contexts. Notably, the process may comprise:

incorporating and dispersing particles, on which at least one free radical captor is immobilized, within molecules or mixtures of molecules to be stabilized;

maintaining said particles within said molecules or mixtures of molecules for their stabilization (at this stage in the method, it can be a case of an intrinsically stable suspension or of a stabilized suspension, for example by agitation or by electrostatic interaction);

physically separating said particles from said molecules or mixtures of molecules for recovering said particles on the one hand, and on the other hand, said molecules or mixtures of molecules, thus rendered sensitive once again to free radicals.

Advantageously, the free radical captors are, in this context, radical polymerization inhibitors or retarders. They intervene temporarily for example within a mixture of monomers during its storage and/or transport. They are then easily removed for example by centrifugation or filtration, prior to carrying out the polymerization of said mixture of monomers.

In other contexts, such radical polymerization inhibitors or retarders are immobilized on recipient walls or on detachable structures. In order to annihilate their inhibitory action with regard to monomers, they are removed from contact with them. In the first case, the monomers are transported away, in the second case said detachable structure is removed.

The person skilled in the art, upon reading the foregoing, has not failed to grasp the interest of the invention. The invention is now illustrated by Examples A and B below.

Within the context of said Examples, various methods of immobilizing radical polymerization inhibitors or retarders onto mineral supports (silica particles) have notably been set forth. For reasons of simplicity, only the term "radical polymerization inhibitor" is spoken of in said Examples. The person skilled in the art cannot ignore that according to the kinetics in question, this term reveals to be suitable or not. In this latter case, it is hereafter advantageously implicitly replaced by the term "radical polymerization retarder".

EXAMPLE A

1) Radical Polymerization Inhibitors

Two types of inhibitor were used:

hydroquinone (HQ): an inhibitor which is frequently used for stabilizing acrylates and methacrylates. After grafting, the active part is of the alkoxyphenol type. The alkoxyphenols such as methoxyphenol (MP) are well known for their inhibiting properties for acrylates;

2,2,6,6-tetramethylpiperidinooxy (TEMPO): a stable organic radical. This radical reacts with C radicals to form covalent bonds which are able to rupture homolytically with heating. Thus, the TEMPO radicals can be regenerated by washing, with a hot solvent, the surfaces on which they were grafted according to the invention. Free radical stabilizing articles may therefore be prepared with these radicals, which are reusable, and which are especially useful in the fields of transport and storage of monomers.

2) Solid Supports

Two types of particles of silica having different particle sizes were used.

For the first type, the weight distribution shows an average diameter of 0.3 $\mu$m (in fact: 10% below 0.088 $\mu$m, 10% above 0.434 $\mu$m and nothing above 0.8 $\mu$m).

For the second type, the weight distribution shows an average diameter of 55 $\mu$m (in fact: 10% below 30 $\mu$m, 10% above 100 $\mu$m).

3) Grafting

In order to carry out tests, the size of the particles was varied thus. The grafting method was also varied, more specifically, the nature of the coupling agent (with the presence or not of a spacer) used between the silica and the inhibitor. In fact, the nature and the size of the coupling agent act upon the mobility of the inhibitor and may influence the efficiency of the inhibition. Two types of grafting were carried out:

a) a "short" grafting between the silica particles and the inhibitor;

b) a "long" grafting, via a flexible spacer between the silica particles and the inhibitor.

a) "Short" Grafting

Clean and dry silica particles were stirred in 10 ml of anhydrous methylene chloride. Silicon tetrachloride (1 ml) was added. Said mixture was then stirred vigorously at ambient temperature for 30 minutes. The stirring was stopped in order to enable decanting the particles. The solvent was removed and the silica particles were washed quickly with anhydrous methylene chloride. 10 ml of anhydrous methylene chloride were then poured on said particles and the inhibitor (1 g) was added. The resulting mixture was stirred for 3 hours, then filtered. The recovered grafted particles were cautiously washed with methylene chloride and ethanol in order to remove traces of non-grafted inhibitor.

Said washed grafted particles were then dried. The grafting generated bonds of the type:

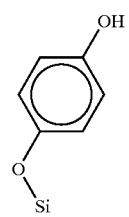

with HQ;

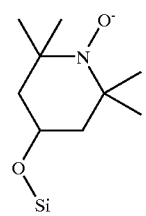

with TEMPO.

b) "Long" Grafting

The same procedure was carried out except that the inhibitor was replaced by bromopropanol (spacer). The silica particles grafted with said bromopropanol were then placed in a flask with 0.5 g of sodium carbonate, 1 g of hydroquinone (HQ), and 20 ml of THF. The resulting mixture was stirred and heated under reflux for 16 hours. It was then brought to ambient temperature. Finally, the mixture was neutralised by adding a 1M solution of hydrochloric acid (HCl). The particles grafted with the entities (coupling agent+spacer)-(hydroquinone) (Si—Sp—HQ) were filtered and washed cautiously with THF and ethanol. They were finally dried.

The grafting with spacer generated bonds of type:

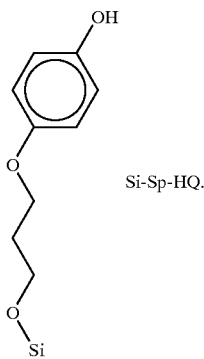

Si-Sp-HQ.

4) Verification of the Inhibiting Power of the Grafted Inhibitors

The stabilizing action of the grafted inhibitors was verified mainly on methyl methacrylate (MMA) monomers.

To this end, in order to simulate the spontaneous formation of free radicals in the mixture, and to accelerate said formation, a thermal radical polymerization initiator, ADVN or 4,4'-azobis-4-cyanovaleric acid was added.

More specifically, it was carried out as follows:

7 different vials (identified as a, b, c, d, e, f, and g) were charged with:

- 5 ml of freshly distilled methyl methacrylate (MMA) (HPLC, $C_8$ reverse phase, eluent: 40% acetonitrile, 60% sodium acetate buffer, electrochemical and UV detectors, methoxyphenol concentration lower than 0.2 ppm, hydroquinone concentration lower than 0.3 ppm);
- 5 mg of ADVN; and
- a magnetic stirrer.

In vial a (respectively b), 1 g of non-grafted silica particles having an average diameter of 0.3 μm (respectively 55 μm) was introduced. In vials c to g, 1 g of silica particles grafted with an inhibitor (HQ, TEMPO or Sp—HQ) was introduced. The Table below indicates specifically the types of particles introduced into said vials a to g.

| Vials | a | b | c | d | e | f | g |
|---|---|---|---|---|---|---|---|
| Particle size (μm) | 0.3 | 55 | 0.3 | 55 | 0.3 | 55 | 55 |
| Grafted inhibitor | — | — | HQ | HQ | TEMPO | TEMPO | Sp-HQ |

Each of the vials was stirred and heated at 60° C. In vials a and b (not containing inhibitor) the monomer (MMA) rapidly polymerised. The viscosity increased and the mixture became solid in 1 h.

In vials c to g, the mixtures remained fluid. They were still fluid after 16 hours at 60° C., even though more than 97% of the initiator had dissociated into free radicals (half life: about 180 minutes at 60° C.).

The grafted inhibitors develop their inhibiting action.

5) Verification of the Stability of the Grafting

Two samples were prepared, as indicated above for the sample of vial g (Si—Sp—HQ on silica particles of 55 μm). They were stirred at ambient temperature. They were filtered and analysed by HPLC (reverse phase $C_8$; eluent: 40% acetonitrile, 60% sodium acetate buffer, electrochemical and UV detectors) after 30 min and 24 h respectively. The hydroquinone content, detectable only by the electrochemical detector, was estimated at less than 0.3 ppm.

Said hydroquinone was grafted in a very stable manner onto the silica particles. The stability of the grafting was verified during reactivity tests at higher temperature.

6) Verification of the Reactivity of the Temporarily Stabilized Monomer

Two vials "of type g" were prepared. Each contain:

- 1 g of grafted silica particles (Sp—HQ on silica particles of 55 μm);
- 10 mg of ADVN;
- 5 ml of monomers (MMA); and
- a magnetic stirrer.

Each of the mixtures was stirred and heated at 60° C. for 1 hour. At the end of this heating, about 20% of the ADVN had decomposed and 80% of this initiator remained non-dissociated (half-life: about 180 min at 60° C.).

The vials were brought to ambient temperature. 2.5 ml was taken from each of said vials, said amount was filtered and poured into two other vials. 2.5 ml of grafted monomer-silica mixture was conserved in the first vials.

The four vials were then stirred and heated at 60° C. for 6 h, during which time 75% of the residual ADVN was dissociated and thus numerous free radicals were formed.

After 2 hours, the filtered samples (in the two other vials) polymerised to generate a solid mass, whereas the samples containing the grafted silica (in the first two vials) remained fluid.

The inoccuousness of the grafted inhibitors of the invention towards the reactivity of the monomers has hereby been verified after their removal by simple filtration, as well as, once again, the efficiency of their inhibiting action.

EXAMPLE B

1) Radical Polymerization Inhibitor

Hydroquinone (HQ) was used.

2) Solid Support

Silica particles marketed by Degussa were used. They had an average diameter of 20 nm.

3) "Long" Grafting

The grafting method was carried out in two steps. First of all, glycidoxypropyl trimethoxysilane (coupling agent with intrinsic spacer: GlyMo) was condensed onto the silica particles. Hydroquinone (HQ) was then added onto the epoxy group. The reaction scheme is indicated below:

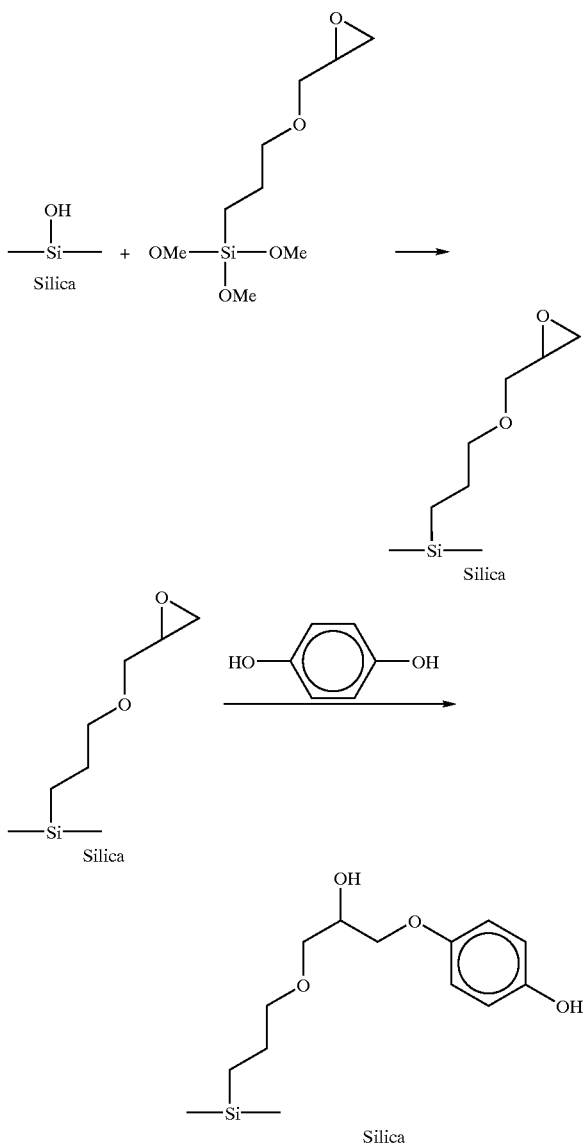

More specifically, the method is carried out as follows:

200 g of a solution of GlyMo (at 1% by weight in THF) are first of all prepared and stirred for 15 minutes. 5 g of the silica particles are added thereto and the resulting mixture is stirred vigorously for 4 hours. After the 4 hours, 5 g of HQ and 0.1 g of potassium tert-butoxide are added. The resulting mixture is heated under reflux and stirred for 16 hours. The majority of the solvent is evaporated off to give a thick paste which is placed in a dialysis membrane tube (pores for stopping particles of a diameter greater than 5 nm). Said tube is placed in a recipient containing 300 ml of THF. The tube is slowly stirred therein for 24 hours. The solvent is then removed and replaced with a further 300 ml of clean THF. The tube is left for 24 hours under slow stirring in this clean THF. The operation is renewed once more. The grafted silica particles are then recovered and dried in vacuo.

4) Verification of the Inhibiting Power of the Grafted Inhibitor

The stabilizing action (with regard to the free radicals) was verified with methyl methacrylate (MMA) monomers. A thermal radical polymerization initiator was added to simulate the spontaneous formation of free radicals in the mixture and to accelerate said formation. The thermal radical polymerization initiator was ADVN or 4,4'-azobis-4-cyanovaleric acid.

Four vials (referenced 1, 2, 3 and 4) were charged with 10 ml of freshly distilled MMA (see Example A), containing less than 0.7 ppm of HQ after distillation (100 ppm before distillation).

Vial 1 was a control vial (without silica particles). In vials 2 and 3, 0.5 g of non-grafted silica particles was added. These also are control vials. In vial 4, 0.5 g of silica particles grafted according to the method described above (grafting of the Sp—HQ type) was added.

At $t_0=0$, samples from the four vials ($1t_0$, $2t_0$, $3t_0$, $4t_0$) were tested. By HPLC, their content of HQ; of methoxyphenol (MP) or other alkoxyphenols were measured (HPLC reverse phase $C_8$; eluent: 40% acetonitrile—60% sodium acetate buffer, electrochemical and UV detectors). No trace of MP or any other alkoxyphenol was detected in the vials. In each one, the HQ content was less than 0.7 ppm.

0.5 mg of ADVN were added into vials 3 and 4. The contents of four vials were then stirred and monitored after 1 hour ($1t_1$, $2t_1$, $3t_1$, $4t_1$).

Said four vials were then heated, with stirring, at 50° C. (half life of the ADNV at 50° C.: about 12 hours). Their content was monitored after:

20 min ($1t_2$, $2t_2$, $3t_2$, $4t_2$); 2% of initiator dissociated, 3 h ($1t_3$, $2t_3$, $3t_3$, $4t_3$); 16% of initiator dissociated, 16 h ($1t_4$, $2t_4$, $3t_4$, 4t4); 54% of initiator dissociated.

The heating with stirring was thus carried out for 16 hours.

More particularly, the viscosities and HQ content of the vials 3 (control with non-grafted silica) and 4 (grafted silica) were considered at $t_1$, $t_2$, $t_3$, and $t_4$. The increase in the viscosity indicated an increase in the level of polymerization of the monomers. The results obtained are given in the Table below.

| Time | Vial 3 | | Vial 4 | |
| --- | --- | --- | --- | --- |
| | HQ conc. | Viscosity | HQ conc. | Viscosity |
| $t_1$ | <0.7 ppm | fluid | <0.7 ppm | fluid |
| $t_2$ | <0.6 ppm | slightly viscous | <0.7 ppm | fluid |
| $t_3$ | <0.6 ppm | highly viscous | <1 ppm | fluid |
| $t_4$ | — | solid | <1 ppm | fluid |

The formation of polyMMA was confirmed by size exclusion chromatography: in the vials 2 and 3 at $t_3$, and in the vials 1, 2 and 3 at $t_4$.

5) Verification of the Stability of the Grafting

No MP or any alkoxyphenol was detected in any of the samples monitored. The HQ concentration was less than 0.7 ppm for all said samples at $t_0=0$. Said HQ concentration remained lower than 0.7 ppm in vials 1 and 2 for all measurement times. At $t_4$, the viscosity of the samples started to increase in vials 1 and 2, and this demonstrates that the non-stabilized monomers started to polymerise even in the absence of the polymerization initiator ADVN.

What is claimed is:

1. A composition comprising:
   a free radical captor immobilized on a solid support; and
   monomers or mixtures of monomers which are sensitive to free radicals, provided that said composition does not contain a polymerization initiator for said monomers or mixtures of monomers and wherein the captor is immobilized on a silica support or a silica-based glass support by chemical grafting, via a coupling agent.

2. The composition according to claim 1, wherein the captor is linked to the silica of said support by a group comprising a chain having at least three atoms which are different from silicon; said group being of the —Si—O—C—C . . . type or of the —Si—C—C—C . . . type.

3. The composition according to claim 1, wherein the coupling agent is a silane coupling agent.

4. The composition according to claim 1, wherein the free radical captor is selected from the group consisting of phenol derivatives, alkoxyphenols, quinones, phenothiazine, stable organic radicals, nitro derivatives, metal salts, and sulphur derivatives.

5. The composition according to claim 1, wherein the free radical captor is selected from the group consisting of hydroquinones, alkoxyphenols, catechols, quinones, phenothiazine, stable organic radicals, nitro derivatives, metal salts, and sulphur derivatives.

6. A composition comprising:
   a free radical captor immobilized on particles; and
   monomers or mixtures of monomers which are sensitive to free radicals.

7. The composition according to claim 6, wherein the captor is immobilized on particles the size of which is between 20 nm and 50 μm and wherein said composition does not contain a polymerization initiator for said monomers or mixtures of monomers.

8. The composition according to claim 6, wherein the captor is immobilized on particles the size of which is between 20 nm and 50 μm.

9. The composition according to claim 6, wherein the free radical captor is selected from the group consisting of phenol derivatives, alkoxyphenols, quinones, phenothiazine, stable organic radicals, nitro derivatives, metal salts, and sulphur derivatives.

10. The composition according to claim 6, wherein the free radical captor is selected from the group consisting of hydroquinones, alkoxyphenols, catechols, quinones, phenothiazine, stable organic radicals, nitro derivatives, metal salts, and sulphur derivatives.

11. A method of stabilizing, at least temporarily, molecules or mixtures of molecules which are sensitive to free radicals, wherein said method comprises:
   incorporating and dispersing particles, on which at least one free radical captor is immobilized, within molecules or mixtures of molecules to be stabilized, wherein said at least one free radical captor is selected from the group consisting of hydroquinones, alkoxyphenols, catechols, quinones, phenothiazine, stable organic radicals, nitro derivatives, metal salts, and sulphur derivatives;
   maintaining said particles within said molecules or mixtures of molecules for their stabilization; and
   physically separating said particles from said molecules or mixtures of molecules for recovering said particles on the one hand and, on the other hand, said molecules or mixtures of molecules thus rendered sensitive once again to free radicals.

12. A method of stabilizing, at least temporarily, monomers or mixtures of monomers which are sensitive to free radicals, wherein said method comprises:
   incorporating and dispersing particles, on which at least one free radical captor is immobilized, within monomers or mixtures of monomers to be stabilized;
   maintaining said particles within said monomers or mixtures of monomers for their stabilization; and
   physically separating said particles from said monomers or mixtures of monomers for recovering said particles on the one hand and, on the other hand, said monomers or mixtures of monomers thus rendered sensitive once again to free radicals.

13. The method according to claim 12, wherein the free radical captor is selected from the group consisting of phenol derivatives, alkoxyphenols, quinones, phenothiazine, stable organic radicals, nitro derivatives, metal salts, and sulphur derivatives.

14. The method according to claim 12, wherein the free radical captor is selected from the group consisting of hydroquinones, alkoxyphnols, catechols, quinones, phenothiazine, stable organic radicals, nitro derivitives, metal salts, and sulphur dertivatives.

15. A method of storing, at least temporarily, monomers or mixtures of monomers which are sensitive to free radicals, wherein said method comprises:
   placing monomers or mixtures of monomers to be stored in contact with a solid support on which at least one free radical captor is immobilized;
   maintaining said solid support in contact with said monomers or mixtures of monomers for their stabilization; and
   physically separating said solid support from said monomers or mixtures of monomers to recover said monomers or mixtures of monomers thus rendered sensitive once again to free radicals.

16. A method according to claim 15, wherein said solid support is a wall of a storage reservoir.

17. A method according to claim 15, wherein said solid support is a detachable structure.

18. A method of transporting monomers or mixtures of monomers which are sensitive to free radicals, wherein said method comprises:
   placing monomers or mixtures of monomers to be transported in contact with a solid support on which at least one free radical captor is immobilized;
   transporting said monomers or mixtures of monomers while maintaining contact between said solid support and said monomers or mixtures of monomers for their stabilization; and
   physically separating said solid support from said monomers or mixtures of monomers to recover said monomers or mixtures of monomers thus rendered sensitive once again to free radicals.

19. A method according to claim 18, wherein said at least one free radical captor is immobilized on a wall of a transport reservoir.

20. A method according to claim 18, wherein said at least one free radical captor is immobilized on piping.

21. A method according to claim 18, wherein said at least one free radical captor is immobilized on a detachable structure.

* * * * *